(12) United States Patent
Ao et al.

(10) Patent No.: US 8,978,476 B2
(45) Date of Patent: Mar. 17, 2015

(54) ULTRASONIC SIGNAL COUPLER

(71) Applicant: General Electric Company, Schenectady, NY (US)

(72) Inventors: Xiaolei Shirley Ao, Lexington, MA (US); Oleg Alexander Khrakovsky, Lynn, MA (US); Yue Ma, Burlington, MA (US)

(73) Assignee: General Electric Company, Schenectady, NY (US)

( * ) Notice: Subject to any disclaimer, the term of this patent is extended or adjusted under 35 U.S.C. 154(b) by 98 days.

(21) Appl. No.: 13/668,909

(22) Filed: Nov. 5, 2012

(65) Prior Publication Data

US 2014/0123767 A1   May 8, 2014

(51) Int. Cl.
G01N 29/28 (2006.01)
G01N 29/24 (2006.01)
G01N 29/04 (2006.01)

(52) U.S. Cl.
CPC ........ *G01N 29/2462* (2013.01); *G01N 29/2468* (2013.01)
USPC ................................. 73/617; 73/622; 73/644

(58) Field of Classification Search
USPC .................... 73/617, 643, 644, 622
See application file for complete search history.

(56) References Cited

U.S. PATENT DOCUMENTS

| | | | |
|---|---|---|---|
| 3,299,695 A * | 1/1967 | Dickinson, III | 73/627 |
| 3,575,050 A | 4/1971 | Lynnworth | |
| 3,940,985 A | 3/1976 | Wyler | |
| 3,973,152 A | 8/1976 | Karplus | |
| 4,286,470 A | 9/1981 | Lynnworth | |
| 4,320,659 A | 3/1982 | Lynnworth et al. | |
| 4,336,719 A | 6/1982 | Lynnworth | |
| 4,373,401 A | 2/1983 | Baumoel | |
| 4,374,477 A | 2/1983 | Kikuchi et al. | |
| 4,532,796 A | 8/1985 | Martens et al. | |
| 4,783,997 A | 11/1988 | Lynnworth | |
| 4,787,252 A | 11/1988 | Jacobson et al. | |
| 5,159,838 A | 11/1992 | Lynnworth | |
| 5,251,490 A * | 10/1993 | Kronberg | 73/861.25 |
| 5,318,035 A | 6/1994 | Konno et al. | |
| 5,349,860 A * | 9/1994 | Nakano et al. | 73/597 |
| 5,440,930 A | 8/1995 | Daire et al. | |
| 5,515,733 A | 5/1996 | Lynnworth | |
| 5,600,073 A | 2/1997 | Hill | |
| 5,719,329 A | 2/1998 | Jepson et al. | |
| 6,047,602 A | 4/2000 | Lynnworth | |
| 6,349,599 B1 | 2/2002 | Lynnworth et al. | |
| 7,343,821 B2 | 3/2008 | Panicke et al. | |
| 2004/0200266 A1 * | 10/2004 | Cardelius et al. | 73/24.01 |
| 2004/0250624 A1 * | 12/2004 | Abbate et al. | 73/597 |
| 2007/0131034 A1 * | 6/2007 | Ehlert et al. | 73/617 |
| 2007/0137312 A1 | 6/2007 | Panicke et al. | |
| 2011/0023623 A1 | 2/2011 | Berberig et al. | |
| 2012/0266679 A1 | 10/2012 | Ao et al. | |

OTHER PUBLICATIONS

Search Report from PCT/US2013/063158 dated Jan. 2, 2014.

* cited by examiner

*Primary Examiner* — Lisa Caputo
*Assistant Examiner* — Rose M Miller
(74) *Attorney, Agent, or Firm* — Hiscock & Barclay LLP

(57) ABSTRACT

An ultrasonic signal coupling assembly including ultrasonic transducers attached to one or more ultrasonic couplers configured to be coupled to an exterior surface of a pipe. A height of the ultrasonic coupler or couplers is greater than a thickness of the pipe by a factor of about five or more, and a length of the ultrasonic coupler or couplers is greater than the height of the ultrasonic coupler or couplers.

17 Claims, 4 Drawing Sheets

ULTRASONIC SIGNAL COUPLER

BACKGROUND OF THE INVENTION

This invention relates generally to ultrasonic flow measurement, and more particularly to an ultrasonic coupler assembly used in the flow measurement.

Ultrasonic flow meters are used to determine the flow rate of a variety of fluids (e.g., liquids, gases, etc.) and combinations of different fluids flowing through pipes of different sizes and shapes. One type of an ultrasonic flow meter employs a transit time method. This technique uses one or more pairs of ultrasonic transducers attached to the exterior of the pipe wall and located upstream and downstream from each other. Each of the transducers, when energized, transmits an ultrasonic signal through the flowing fluid that is detected by the other ultrasonic transducer of the pair. The velocity of the fluid flowing in the pipe can be calculated as a function of the differential transit time of ultrasonic signals as between (1) the ultrasonic signal traveling upward against the fluid flow direction from the downstream ultrasonic transducer to the upstream ultrasonic transducer, and (2) the ultrasonic signal traveling downward with the fluid flow direction from the upstream ultrasonic transducer to the downstream ultrasonic transducer.

The pair(s) of transducers can be mounted on the pipe at different relative locations, for example, the pairs of transducers can be located on opposite sides of the pipe, i.e. diametrically opposed, such that a straight line connecting the transducers passes through the pipe axis, or they can be located adjacently on the same side of the pipe. In the diametric example, the ultrasonic signal transmitted by one of the transducers in the pair of transducers is not reflected off of an interior pipe surface before it is detected by the other transducer in the pair. In the latter example of adjacent transducers, the ultrasonic signal transmitted by one of the transducers in the pair of transducers is reflected by an interior surface of the pipe before it is detected by the other transducer in the pair.

In some applications, the pipes to which the ultrasonic flow meters are attached carry fluids that cause the pipe walls to reach relatively high temperatures, or the pipes may carry fluids that cause the pipe wall to reach relatively low temperatures. An ultrasonic transducer consistently exposed to extreme or varying temperatures introduces thermal stresses that diminish the useful life of the transducer. A coupler positioned between the transducer and the pipe helps to prevent the extreme temperatures from damaging the piezoelectric material. The signal quality can decline due to poor acoustic coupling between the coupler and the pipe wall caused by, for example, use of manual temporary attachment methods, or by deterioration of the piezoelectric material in the transducer caused by exposure to harsh environments such as temperature extremes. Measurements of fluid flow rates through pipes incorporate pipe thickness, the speed of ultrasonic signals traveling through the pipe, interior pipe diameter, and the speed of ultrasonic signals traveling through fluids in the pipe. Because the speed of ultrasonic signals traveling through these materials (pipe and fluid) are different, such measurements can be compromised if the pipe is subject to corrosion that reduces a thickness of the pipe. An ultrasonic signal time measurement of such a pipe could be mistakenly attributed to travel time through the pipe when, in fact, it should be attributed to travel time through the fluid, and so can distort a fluid flow rate calculation.

The discussion above is merely provided for general background information and is not intended to be used as an aid in determining the scope of the claimed subject matter.

BRIEF DESCRIPTION OF THE INVENTION

An ultrasonic signal coupling assembly is disclosed that includes ultrasonic transducers attached to one or more ultrasonic couplers configured to be coupled to an exterior surface of a pipe. A height of the ultrasonic coupler or couplers is greater than a thickness of the pipe by a factor of about five or more, and a length of the ultrasonic coupler or couplers is greater than the height of the ultrasonic coupler or couplers. Advantages that may be realized in the practice of some disclosed embodiments of the ultrasonic signal coupling assembly include an effective thickening of the pipe wall such that corrosive thinning of the pipe wall will not diminish accuracy of flow rate measurement, isolating ultrasonic transducers from temperature extremes, and simplifying aligning and mounting the coupler along chordal locations on the pipe.

In one embodiment, an ultrasonic coupler assembly comprises a first ultrasonic coupler configured to be coupled to an exterior surface of a pipe at a first location. The ultrasonic coupler has a first dimension that is greater than a thickness of the pipe by a factor of at least five, and a second dimension transverse to the first dimension that is greater than the first dimension. A first ultrasonic transducer is attached to the first ultrasonic coupler. A second ultrasonic coupler is configured to be coupled to the exterior surface of the pipe at a second location. The second ultrasonic coupler has a first dimension that is greater than the thickness of the pipe by a factor of about five or more, and a second dimension transverse to the first dimension that is greater than the first dimension. A second ultrasonic transducer is attached to the second ultrasonic coupler.

In another embodiment, an ultrasonic coupler assembly comprises a coupler having a top side and a bottom side. The bottom side is configured to be coupled to an exterior surface of a pipe. The top side has at least one ultrasonic transducer attached to it. A first dimension of the coupler is greater than a thickness of the pipe by a factor of at least five, and a length of the bottom side is greater than the first dimension.

In another embodiment, an ultrasonic coupling system comprises a plurality of pairs of couplers. The first side of each coupler is configured to be coupled to an exterior surface of a pipe. A plurality of ultrasonic transducers are attached to the second side of the couplers. The ultrasonic transducers that are coupled to paired couplers are configured to emit and receive ultrasonic signals between themselves. The distance between the first and second sides of the couplers is less than a length of their first side.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
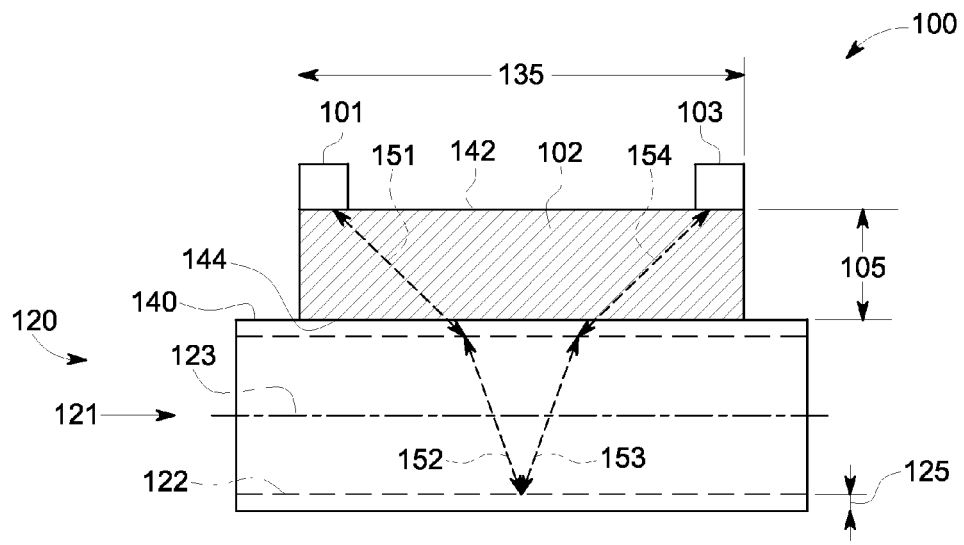
FIG. 1 is a front view of an exemplary ultrasonic coupler system.
Figure 2:
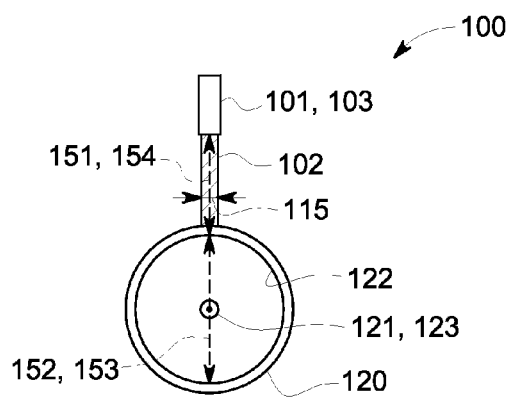
FIG. 2 is a side view of the exemplary ultrasonic coupler system of FIG. 1.

FIG. 1 and FIG. 2 illustrate a front and side view, respectively, of one embodiment of an ultrasonic coupler assembly 100, wherein ultrasonic transducers 101, 103, are attached to ultrasonic coupler 102, which, in turn, is attached to a pipe 120 carrying a fluid traveling in direction 121 therethrough, shown as traveling from left to right in the front view of FIG. 1. The ultrasonic transducers 101, 103 each transmit ultrasonic signals that travel along a representative ultrasonic signal path segment 151, 152, 153, 154, from each of the ultrasonic transducers 101, 103 to the other.

Each of the ultrasonic transducers 101, 103 is capable of emitting ultrasonic signals and detecting ultrasonic signals. For example, when ultrasonic transducer 101 emits an ultrasonic signal it travels along representative ultrasonic signal path segment 151 through the ultrasonic coupler 102 and pipe 120, then is refracted along representative ultrasonic signal path segment 152 by a fluid traveling through the pipe 120, then is reflected off of interior surface 122 of the pipe 120 along representative ultrasonic signal path segment 153, then is refracted by the pipe 120 along representative ultrasonic signal path segment 154 through the pipe 120 and ultrasonic coupler 102 whereby the ultrasonic signal emitted by ultrasonic transducer 101 is detected by ultrasonic transducer 103.

Similarly, when ultrasonic transducer 103 emits an ultrasonic signal it travels along representative ultrasonic signal path segment 154 through the ultrasonic coupler 102 and pipe 120, then is refracted along representative ultrasonic signal path segment 153 by a fluid traveling through the pipe 120, then is reflected off of interior surface 122 of the pipe 120 along representative ultrasonic signal path segment 152, then is refracted by pipe 120 along representative ultrasonic signal path segment 151 through the pipe 120 and ultrasonic coupler 102 whereby the ultrasonic signal emitted by ultrasonic transducer 103 is detected by ultrasonic transducer 101. In one embodiment, ultrasonic coupler 102 is welded in place for providing high quality acoustic coupling between the ultrasonic coupler 102 and the pipe 120. In another embodiment, ultrasonic coupler 102 is mounted on pipe 120 using clamps. In either of these embodiments, the ultrasonic coupler 102 can be made of the same or different material as the pipe 120. The ultrasonic coupler 102 can be integrally formed with pipe 120 and be made of the same material as the pipe 120 in an extrusion based fabrication process, or it can be molded into pipe 120 using the same material as the pipe in a casting fabrication process.

In the embodiment shown in FIG. 1 and FIG. 2, the rectangular shaped ultrasonic coupler 102 comprises a top surface 142 and a bottom surface 144 and an ultrasonic coupler height 105 as measured by a line that is normal to both the top surface 142 and the bottom surface 144 of the ultrasonic coupler 102. The ultrasonic coupler 102 is not limited to a rectangular shape, as depicted in FIGS. 1-2, and can also comprise a rhomboid or trapezoid shape. In one embodiment, described herein, the top surface 142 and the bottom surface 144 are parallel. The ultrasonic transducers 101, 103 are mounted on the top surface 142 of the ultrasonic coupler 102. The ultrasonic coupler 102 also comprises an ultrasonic coupler length 135 and width 115. The ultrasonic coupler 102 is aligned on an exterior surface 140 of the pipe 120 along its length 135, i.e. the long side of its rectangular shape, in parallel with an axis 123 of the pipe 120. In one embodiment, the bottom surface 144 of the ultrasonic coupler 102 in contact with pipe 120 is shaped to match the curvature of the pipe 120. In the embodiment shown in FIG. 1 and FIG. 2, the ultrasonic transducers 101, 103, are disposed in an adjacent, same side configuration on one ultrasonic coupler 102. In one embodiment the ultrasonic coupler 102 is made from the same material as the pipe 120, such as carbon steel, stainless steel, or titanium. The ultrasonic transducers 101, 103 can comprise longitudinal ultrasonic transducers and shear wave ultrasonic transducers. In a shear wave embodiment, ultrasonic transducers 101, 103 can include ultrasonic transducers mounted on a wedge for inducing shear wave refraction between the wedge material and the ultrasonic coupler 102. In either case, representative ultrasonic signal path segments 151 and 154 represent the ultrasonic signals emitted by either a longitudinal ultrasonic transducer or a shear wave ultrasonic transducer.

In one embodiment, the ultrasonic coupler 102 is in contact with pipe 120 along the full length 135 of the ultrasonic coupler 102 for providing high quality acoustic coupling between the ultrasonic coupler 102 and the pipe 120. An increased contact area of the ultrasonic coupler 102 and the pipe 120 improves fluid flow rate measurement accuracy. A thickness 125 of pipe 120 typically ranges from about 3 mm to 10 mm and a width 115 of the ultrasonic coupler 102 can vary from about 6 mm to 13 mm. Each of the ultrasonic transducers 101, 103 are electronically connected to an ultrasonic processing system (not shown) which controls the ultrasonic signals emitted by the ultrasonic transducer 101, 103 and processes the ultrasonic signals received by the ultrasonic transducers 101, 103. The time duration between ultrasonic transducer 101 emitting the ultrasonic signal and ultrasonic transducer 103 detecting the ultrasonic signal, and vice versa, is measured by the ultrasonic processing system and is referred to as a time-of-flight measurement herein.

As described above, the time-of-flight measurement for an ultrasonic signal traveling from ultrasonic transducer 101 downstream to ultrasonic transducer 103 will be shorter than the time-of-flight measurement for an ultrasonic signal traveling upstream from ultrasonic transducer 103 to 101 so long as fluid is traveling through the pipe 120 in direction 121 during the time-of-flight measurement. This is because the fluid traveling through the pipe 120 is an ultrasonic sound carrying medium. Therefore, ultrasonic signals passing through the fluid in a downstream direction, e.g. from ultrasonic transducer 101 to ultrasonic transducer 103, travel faster than ultrasonic signals passing through the fluid in an upstream direction, e.g. from ultrasonic transducer 103 to ultrasonic transducer 101. The ultrasonic processing system detects this differential time-of-flight measurement to determine a speed of fluid flow through the pipe 120 in direction 121. The faster the fluid flows through pipe 120 the greater the detected time difference. A precise correspondence is determined between the flow rate and a magnitude of the differential time-of-flight measurement and is used by the ultrasonic processing system for flow rate determination. Some of the variables that affect time-of-flight measurement include materials used for the pipe 120 and ultrasonic coupler 102, the physical dimensions of the pipe 120 and ultrasonic coupler 102, and the type of fluid traveling through the pipe 120. In the configuration as illustrated in FIG. 1 and FIG. 2, the ultrasonic transducers 101, 103 can be replaced by dismounting an old ultrasonic transducer and remounting a new one without requiring a shutdown of the fluid flow systems that utilize pipe 120.

The thickness 125 of pipe 120 can deteriorate over time due to, for example, corrosion of the interior surface 122. Such thinning of pipe 120 can affect the sensitivity of ultrasonic fluid flow rate measurements because ultrasonic signals travel at different speeds through the pipe material and through the fluid in the pipe, as explained above. For example, the effect on the transit time contributed by the pipe thickness 125 is proportional to the pipe thickness 125 divided by the height 105 of the ultrasonic coupler 102. Thus, the ratio of pipe thickness 125 to ultrasonic coupler height 105 should be minimized to the extent that changes in pipe thickness 125 will significantly affect flow rate measurements. Therefore, a height 105 of the ultrasonic coupler 102 is predesigned to be greater than a thickness of the pipe 125 to minimize the effects of pipe corrosion on the measured transit time of an ultrasonic signal traveling between the ultrasonic transducers 101, 103. Ultrasonic coupler height 105 can be preselected to be, for example, about 5× through about 15× the pipe thickness 125. This will reduce the impact of corrosion in the pipe 120 on the flow rate measurement by the same proportion (about 5× through about 15×) as compared to a flow rate measurement configuration without an ultrasonic coupler 102. A key benefit of the ultrasonic coupler 102 is the ability to weld it to pipe 120 to increase an effective thickness of the pipe 120 with respect to ultrasonic flow rate measurements.

Figure 3:
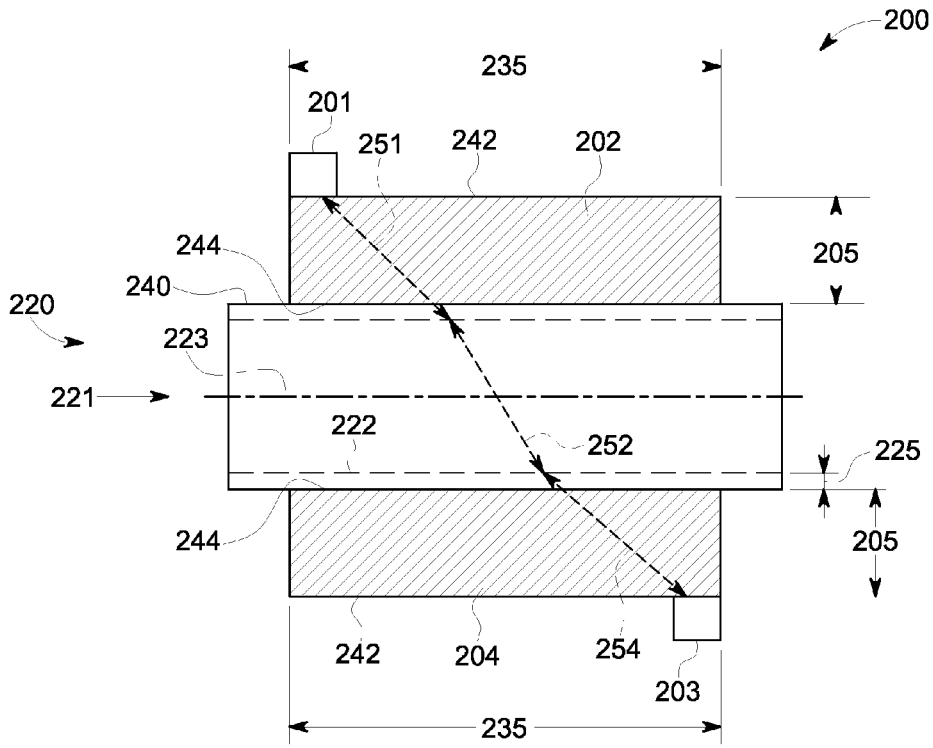
FIG. 3 is a front view of an exemplary diametric ultrasonic coupler system.
Figure 4:
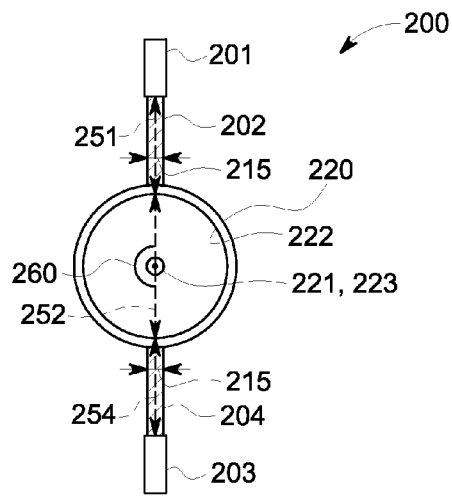
FIG. 4 is a side view of the exemplary diametric ultrasonic coupler system of FIG. 3.

FIG. 3 and FIG. 4 illustrate a front and side view, respectively, of one embodiment of an ultrasonic coupler assembly 200, wherein ultrasonic transducers 201, 203, are each attached to a separate ultrasonic coupler 202, 204, respectively, which, in turn, are attached to a pipe 220 carrying a fluid traveling in direction 221 therethrough, shown as traveling from left to right in the front view of FIG. 3. The ultrasonic transducers 201, 203 each transmit ultrasonic signals that travel along a representative ultrasonic signal path comprising segments 251, 252, 254, from each of the ultrasonic transducers 201, 203 to the other. Each of the ultrasonic transducers 201, 203 is capable of emitting ultrasonic signals and detecting ultrasonic signals.

For example, when ultrasonic transducer 201 emits an ultrasonic signal it travels along representative ultrasonic signal path segment 251 through the ultrasonic coupler 202 and pipe 220, then is refracted along representative ultrasonic signal path segment 252 by the fluid traveling through the pipe 220, then is refracted by pipe 220 along representative ultrasonic signal path segment 254 through pipe 220 and ultrasonic coupler 204 whereby the ultrasonic signal emitted by ultrasonic transducer 201 is detected by ultrasonic transducer 203. Similarly, when ultrasonic transducer 203 emits an ultrasonic signal it travels along representative ultrasonic signal path segment 254 through the ultrasonic coupler 204 and pipe 220, then is refracted along representative ultrasonic signal path segment 252 by the fluid traveling through the pipe 220, then is refracted by pipe 220 along representative ultrasonic signal path segment 251 through the pipe 220 and ultrasonic coupler 202 whereby the ultrasonic signal emitted by ultrasonic transducer 203 is detected by ultrasonic transducer 201.

In one embodiment, ultrasonic couplers 202, 204 are welded in place for providing high quality acoustic coupling between the ultrasonic couplers 202, 204 and the pipe 220. Ultrasonic couplers 202, 204 can also be mounted on pipe 220 using clamps. In either of these embodiments, the ultrasonic couplers 202, 204 can be made of the same or different material as the pipe 220. The ultrasonic couplers can be integrally formed with pipe 220 using an extrusion based fabrication process or they can be molded into pipe 220 using a casting fabrication process. In the latter two embodiments, the ultrasonic couplers 202, 204 are made of the same material as the pipe 220. In some applications, this direct detection path, i.e. a non-reflected path as compared with the reflected path example of FIG. 1 and FIG. 2, is preferred because the signal path is shorter. This preference would depend upon pipe 220 diameter, i.e. distance traveled by the ultrasonic signal and ultrasonic signal attenuation over such a path, as well as other variables such as type of fluid traveling through the pipe 220.

In the embodiment shown in FIG. 3 and FIG. 4, the rectangular shaped ultrasonic couplers 202, 204, each comprise a top surface 242 and a bottom surface 244 and an ultrasonic coupler height 205 as measured by a line that is normal to both the top surface 242 and the bottom surface 244 of each of the ultrasonic couplers 202, 204. The ultrasonic couplers 202, 204 are not limited to a rectangular shape or to having the same size, as depicted in the embodiment of FIGS. 3-4, and can also comprise a rhomboid or trapezoid shape or a different size. In one embodiment, the top surfaces 242 and the bottom surfaces 244 are parallel. The ultrasonic transducers 201, 203 are mounted on the top surface 242 of the ultrasonic couplers 202, 204. The ultrasonic couplers 202, 204, each also comprise an ultrasonic coupler length 235 and width 215. The ultrasonic couplers 202, 204 are in contact with pipe 220 along their full lengths 235 and are aligned on an exterior surface 240 of the pipe 220 in parallel with an axis 223 of the pipe 220. In one embodiment, the bottom surfaces 244 of the ultrasonic couplers 202, 204 in contact with pipe 220 are shaped to match the curvature of the pipe 220. This provides high quality acoustic coupling between ultrasonic couplers 202, 204 and the pipe 220. Increasing the contact area of the ultrasonic couplers 202, 204 and the pipe 220 improves fluid flow rate measurement accuracy. A thickness 225 of pipe 220 typically ranges from about 3 mm to 10 mm and a width 215 of the ultrasonic couplers 202, 204 can vary from about 6 mm to 13 mm.

In one embodiment the ultrasonic couplers 202, 204 are made from the same material as the pipe 220, such as carbon steel, stainless steel, or titanium. The ultrasonic transducers 201, 203 can comprise longitudinal ultrasonic transducers and shear wave ultrasonic transducers. Thus, the ultrasonic transducers 201, 203 can include ultrasonic transducers mounted on a wedge for inducing shear wave refraction between the wedge material and the ultrasonic couplers 202, 204. In either case, representative ultrasonic signal path segments 251, 254 represent the ultrasonic signals emitted thereby. In the embodiment shown in FIG. 3 and FIG. 4, the ultrasonic couplers 202, 204, are disposed in a diametric configuration using two ultrasonic couplers 202, 204. Therefore, the ultrasonic couplers 202, 204, are separated by 180° as measured by the angle formed by a midpoint of the location where ultrasonic coupler 202 contacts pipe 220, the central pipe axis 223, and a midpoint of the location where ultrasonic coupler 204 contacts pipe 220.

In one embodiment the ultrasonic couplers 202, 204 are made from the same material as the pipe 220, such as carbon steel, stainless steel, or titanium. The ultrasonic transducers 201, 203 can comprise longitudinal ultrasonic transducers and shear wave ultrasonic transducers. Thus, the ultrasonic transducers 201, 203 can include ultrasonic transducers mounted on a wedge for inducing shear wave refraction between the wedge material and the ultrasonic couplers 202, 204. In either case, representative ultrasonic signal path segments 251, 254 represent the ultrasonic signals emitted thereby. In the embodiment shown in FIG. 3 and FIG. 4, the ultrasonic couplers 202, 204, are disposed in a diametric configuration using two ultrasonic couplers 202, 204. Therefore, the ultrasonic couplers 202, 204, are separated by 180° as measured by the angle 260 formed by a midpoint of the location where ultrasonic coupler 202 contacts pipe 220, the central pipe axis 223, and a midpoint of the location where ultrasonic coupler 204 contacts pipe 220.

As described above, the time-of-flight measurement for an ultrasonic signal traveling from ultrasonic transducer 201 to ultrasonic transducer 203 will be shorter than the time-of-flight measurement for an ultrasonic signal traveling from ultrasonic transducer 203 to 201 so long as fluid is traveling through the pipe 220 in direction 221 during the time-of-flight measurement. This is because the fluid traveling through the pipe 220 is an ultrasonic sound carrying medium. Therefore, ultrasonic signals passing through the fluid in a downstream direction, e.g. from ultrasonic transducer 201 to ultrasonic transducer 203, travel faster than ultrasonic signals passing through the fluid in an upstream direction, e.g. from ultrasonic transducer 203 to ultrasonic transducer 201. The ultrasonic processing system detects this differential time-of-flight measurement to determine a speed of fluid flow through the pipe 220 in direction 221. The faster that the fluid flows through pipe 220 the greater the detected time difference. A precise correspondence is determined between the flow rate and a magnitude of the differential time-of-flight measurement and is used by the ultrasonic processing system for flow rate determination. Some of the variables that affect time-of-flight measurement include materials used for, and physical dimensions of, the pipe 220 and ultrasonic couplers 202, 204, and the type of fluid traveling through the pipe 220. In the configuration as illustrated in FIG. 3 and FIG. 4, the ultrasonic transducers 201, 203 can be replaced by dismounting an old ultrasonic transducer and remounting a new one without requiring a shutdown of the fluid flow systems that utilizes pipe 220.

The thickness 225 of pipe 220 can deteriorate over time due to, for example, corrosion of the interior surface 222. Such thinning of pipe 220 can affect the results of ultrasonic fluid flow rate measurements because ultrasonic signals travel at different speeds through the pipe material and through the fluid in the pipe, as explained above. For example, the effect on the transit time contributed by the pipe thickness 225 is proportional to the pipe thickness 225 divided by the height 205 (225/205) of the ultrasonic couplers 202, 204. Thus, the ratio of pipe thickness 225 to a height 205 of the ultrasonic couplers 202, 204 should be minimized to the extent that changes in pipe thickness 225 will significantly affect flow rate measurements. Therefore, a height 205 of the ultrasonic couplers 202, 204 is predesigned to be greater than a thickness 225 of the pipe 220 to minimize the effects of pipe corrosion on the measured transit time of an ultrasonic signal traveling between the ultrasonic transducers 201, 202. The height 205 of the ultrasonic couplers 202, 204 can be preselected to be, for example, 5× through 15× the pipe thickness 225. This will reduce the effect of corrosion in the pipe 220 on the flow rate measurement by the same proportion (5× through 15×) as compared to a flow rate measurement configuration without ultrasonic couplers 202, 204. A key benefit of the ultrasonic couplers 202, 204 is the ability to weld them to pipe 220 to increase an effective thickness of the pipe 220 with respect to ultrasonic flow rate measurements.

Figure 5:
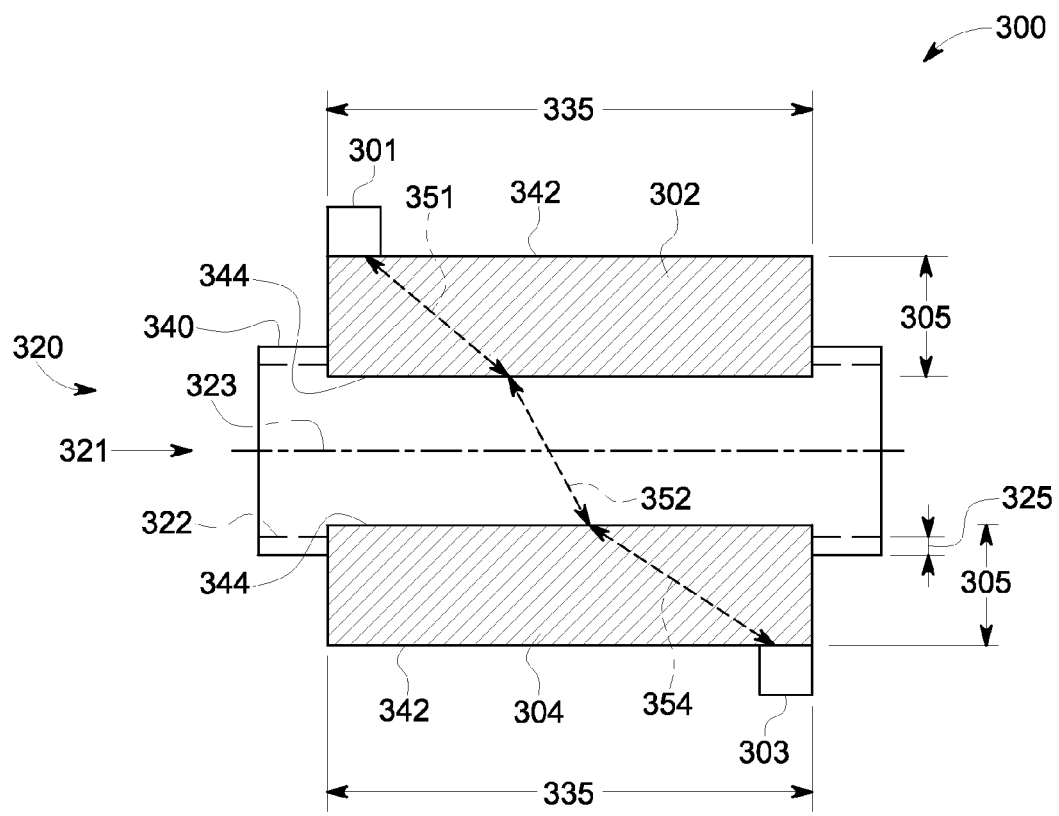
FIG. 5 is a front view of an exemplary chordal ultrasonic coupler system.
Figure 6:
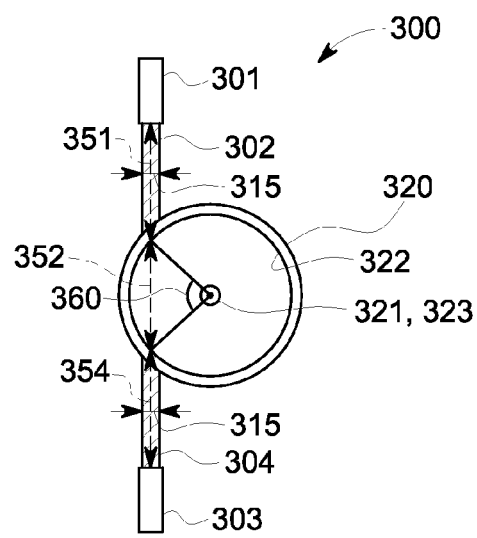
FIG. 6 is a side view of the exemplary chordal ultrasonic coupler system of FIG. 5.

FIG. 5 and FIG. 6 illustrate a front and side view, respectively, of one embodiment of an ultrasonic coupler assembly 300, wherein ultrasonic transducers 301, 303, are each attached to a separate ultrasonic coupler 302, 304, respectively, which, in turn, are attached to a pipe 320 carrying a fluid traveling in direction 321 therethrough, shown as traveling from left to right in the front view of FIG. 5. The ultrasonic transducers 301, 303 each transmit ultrasonic signals that travel along a representative ultrasonic signal path comprising segments 351, 352, 354, from each of the ultrasonic transducers 301, 303 to the other. Each of the ultrasonic transducers 301, 303 is capable of emitting ultrasonic signals and detecting ultrasonic signals. For example, when ultrasonic transducer 301 emits an ultrasonic signal it travels along representative ultrasonic signal path segment 351 through the ultrasonic coupler 302 and pipe 320, then is refracted along representative ultrasonic signal path segment 352 by the fluid traveling through the pipe 320, then is refracted by pipe 320 along representative ultrasonic signal path segment 354 through pipe 320 and ultrasonic coupler 304 whereby the ultrasonic signal emitted by ultrasonic transducer 301 is detected by ultrasonic transducer 303.

Similarly, when ultrasonic transducer 303 emits an ultrasonic signal it travels along representative ultrasonic signal path segment 354 through the ultrasonic coupler 304 and pipe 320, then is refracted along representative ultrasonic signal path segment 352 by the fluid traveling through the pipe 320, then is refracted by pipe 320 along representative ultrasonic signal path segment 351 through the pipe 320 and ultrasonic coupler 302 whereby the ultrasonic signal emitted by ultrasonic transducer 303 is detected by ultrasonic transducer 301. In one embodiment, ultrasonic couplers 302, 304 are welded in place for providing high quality acoustic coupling between the ultrasonic couplers 302, 304 and the pipe 320. In another embodiment, ultrasonic couplers 302, 304 are mounted on pipe 320 using clamps. In either of these embodiments, the ultrasonic couplers 302, 304 can be made of the same or different material as the pipe 320. The ultrasonic couplers 302, 304 can be integrally formed with pipe 320 and be made of the same material as the pipe 320 in an extrusion based fabrication process, or it can be molded into pipe 320 using the same material as the pipe in a casting fabrication process.

In the embodiment shown in FIG. 5 and FIG. 6, the rectangular shaped ultrasonic couplers 302, 304, each comprise a top surface 342 and a bottom surface 344 and an ultrasonic coupler height 305 as measured by a line that is normal to both the top surface 342 and the bottom surface 344 of the ultrasonic couplers 302, 304. The ultrasonic couplers 302, 304 are not limited to a rectangular shape or to having the same size, as depicted in the embodiment of FIGS. 5-6, and can also comprise a rhomboid or trapezoid shape or a different size. In one embodiment, the top surfaces 342 and the bottom surfaces 344 are parallel. The ultrasonic transducers 301, 303 are mounted on the top surfaces 342 of the ultrasonic couplers 302, 304. The ultrasonic couplers 302, 304, each also comprise an ultrasonic coupler length 335 and width 315. The ultrasonic couplers 302, 304 are in contact with pipe 320 along their full lengths 335 and are aligned on an exterior surface 340 of the pipe 320 in parallel with an axis 323 of the pipe 320. In one embodiment, the bottom surfaces 344 of the ultrasonic couplers 302, 304 in contact with pipe 320 are shaped to match the curvature of the pipe 320. This provides high quality acoustic coupling between ultrasonic couplers 302, 304 and the pipe 320. Increasing the contact area of the ultrasonic couplers 302, 304 and the pipe 320 improves fluid flow rate measurement accuracy. A thickness 325 of pipe 320 typically ranges from about 3 mm to 10 mm and a width 315 of the ultrasonic couplers 302, 304 can vary from about 6 mm to 13 mm.

In one embodiment the ultrasonic couplers 302, 304 are made from the same material as the pipe 320, such as carbon steel, stainless steel, or titanium. The ultrasonic transducers 301, 303 can comprise longitudinal ultrasonic transducers and shear wave ultrasonic transducers. Thus, the ultrasonic transducers 301, 303 can include ultrasonic transducers mounted on a wedge for inducing shear wave refraction between the wedge material and the ultrasonic couplers 302, 304. In either case, representative ultrasonic signal path segments 351, 354 represent the ultrasonic signals emitted thereby. In the embodiment shown in FIG. 5 and FIG. 6, the ultrasonic couplers 302, 304, are disposed in a chordal configuration using two ultrasonic couplers 302, 304. Therefore, the ultrasonic couplers 302, 304, are separated by an angle 360 that is less than 180° as measured by the angle formed by a midpoint of the location where ultrasonic coupler 302 contacts pipe 320, the central pipe axis 323, and a midpoint of the location where ultrasonic coupler 304 contacts pipe 320.

Each of the ultrasonic transducers 301, 303 are electronically connected to an ultrasonic processing system (not shown) which controls the ultrasonic signals emitted by the ultrasonic transducers 301, 303 and processes the detected ultrasonic signals received by the ultrasonic transducers 301, 303. The time-of-flight measurement between, for example, ultrasonic transducer 301 emitting the ultrasonic signal and ultrasonic transducer 303 detecting the ultrasonic signal, and vice versa, is performed by the ultrasonic processing system.

As described above, the time-of-flight measurement for an ultrasonic signal traveling from ultrasonic transducer 301 to ultrasonic transducer 303 will be shorter than the time-of-flight measurement for an ultrasonic signal traveling from ultrasonic transducer 303 to 301 so long as fluid is traveling through the pipe 320 in direction 321 during the time-of-flight measurement. This is because the fluid traveling through the pipe 320 is an ultrasonic sound carrying medium. Therefore, ultrasonic signals passing through the fluid in a downstream direction, e.g. from ultrasonic transducer 301 to ultrasonic transducer 303, travel faster than ultrasonic signals passing through the fluid in an upstream direction, e.g. from ultrasonic transducer 303 to ultrasonic transducer 301. The ultrasonic processing system detects this differential time-of-flight measurement to determine a speed of fluid flow through the pipe 320 in direction 321. The faster that the fluid flows through pipe 320 the greater the detected time difference. A precise correspondence is determined between the flow rate and a magnitude of the differential time-of-flight measurement and is used by the ultrasonic processing system for flow rate determination. Some of the variables that affect time-of-flight measurement include materials used for, and physical dimensions of, the pipe 320 and ultrasonic couplers 302, 304, and the type of fluid traveling through the pipe 320. In the configuration as illustrated in FIG. 5 and FIG. 6, the ultrasonic transducers 301, 303 can be replaced by dismounting an old ultrasonic transducer and remounting a new one without requiring a shutdown of the fluid flow systems that utilizes pipe 320.

The thickness 325 of pipe 320 can deteriorate over time due to, for example, corrosion of the interior surface 322. Such thinning of pipe 320 can affect the results of ultrasonic fluid flow rate measurements because ultrasonic signals travel at different speeds through the pipe material and through the fluid in the pipe, as explained above. For example, the effect on the transit time contributed by the pipe thickness 325 is proportional to the pipe thickness 325 divided by the height 305 (325/305) of the ultrasonic couplers 302, 304. Thus, the ratio of pipe thickness 325 to a height 305 of the ultrasonic couplers 302, 304 should be minimized to the extent that changes in pipe thickness 325 will significantly affect flow rate measurements. Therefore, a height 305 of the ultrasonic couplers 302, 304 is predesigned to be greater than a thickness 325 of the pipe 320 to minimize the effects of pipe corrosion on the measured transit time of an ultrasonic signal traveling between the ultrasonic transducers 301, 302. The height 305 of the ultrasonic couplers 302, 304 can be preselected to be, for example, 5× through 15× the pipe thickness 325. This will reduce the magnitude of errors induced in the flow rate measurement, caused by corrosion, in the same proportion (5× through 15×) as compared to a flow rate measurement configuration without ultrasonic couplers 302, 304. One benefit of the ultrasonic couplers 302, 304 is the ability to weld them to pipe 320 to increase an effective thickness of the pipe 320 with respect to ultrasonic flow rate measurements.

Figure 7:
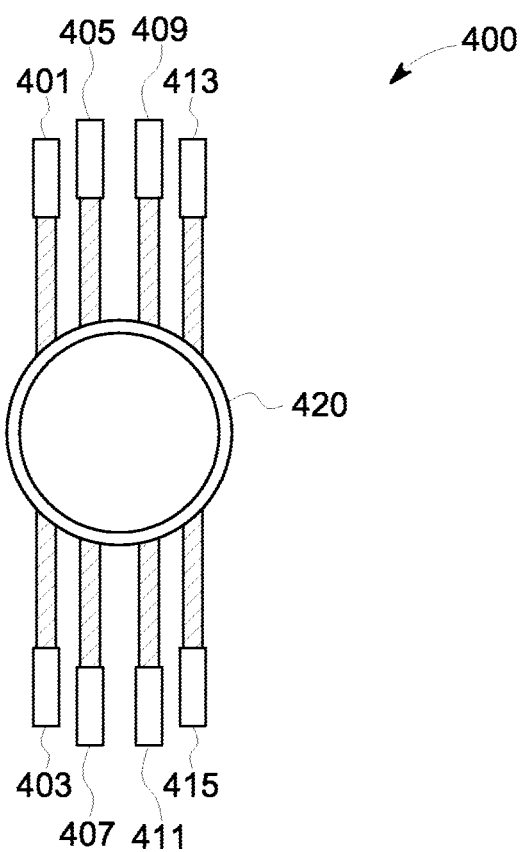
FIG. 7 is a side view of an exemplary multiple chordal ultrasonic coupler system.

FIG. 7 illustrates an alternative embodiment of an ultrasonic flow metering system 400 wherein four pairs of ultrasonic transducers/couplers 401 and 403, 405 and 407, 409 and 411, and 413 and 415, are acoustically coupled to pipe 420, wherein each transducer pair operates as described above with reference to FIG. 5 and FIG. 6.

In view of the foregoing, embodiments of the invention serve to distance the ultrasonic transducer from harsh environments caused by temperature variations and to increase an effective thickness of a pipe for fluid flow rate measurements. A technical effect is to enable non-destructive testing and accurate fluid flow rate measurement at extreme temperatures and under corrosive conditions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic coupler assembly comprising:
  a coupler having a top side and a bottom side opposite the top side, the bottom side configured to be coupled to an exterior of a wall of a pipe and the top side for coupling at least one ultrasonic transducer thereto, the coupler having a height, as measured from the top side to the bottom side, that is greater than a thickness of the pipe by a factor of at least five, a length of the bottom side of the coupler being greater than the height of the coupler.

2. The ultrasonic coupler assembly of claim 1, wherein the coupler is made from a same material as the pipe.

3. The ultrasonic coupler assembly of claim 2, wherein the coupler is made from titanium, carbon steel, stainless steel, or a combination thereof.

4. The ultrasonic coupler assembly of claim 1, wherein the first dimension is greater than the thickness of the pipe by a factor between five to about fifteen.

5. The ultrasonic coupler assembly of claim 1, wherein the top side of the coupler comprises a plurality of ultrasonic transducers coupled thereto, and wherein each of the plurality of ultrasonic transducers emits ultrasonic signals that are detected by another one of the plurality of ultrasonic transducers.

6. The ultrasonic coupler assembly of claim 1, wherein a longer dimension of the bottom surface of the coupler is parallel with a longitudinal axis of the pipe.

7. An ultrasonic coupler assembly comprising:
a first ultrasonic coupler configured to be coupled to an exterior of a wall of a pipe at a first location, wherein a height of the first ultrasonic coupler, as measured between first and second surfaces thereof, is greater than a thickness of the pipe by a factor of at least five, a length transverse to the height of the first ultrasonic coupler is greater than the height of the first ultrasonic coupler, and the second surface of the first ultrasonic coupler is configured to contact the pipe along the full length thereof;
a first ultrasonic transducer attached to the first surface of the first ultrasonic coupler;
a second ultrasonic coupler configured to be coupled to the exterior of the wall of the pipe at a second location, wherein a height of the second ultrasonic coupler, as measured between first and second surfaces thereof, is greater than the thickness of the pipe by a factor of at least five, a length of the second ultrasonic coupler transverse to the height of the second ultrasonic coupler is greater than the height of the second ultrasonic coupler, and the second surface of the first ultrasonic coupler is configured to contact the pipe along the full length thereof; and
a second ultrasonic transducer attached to the first surface of the second ultrasonic coupler.

8. The ultrasonic coupler assembly of claim 7, wherein the first and second ultrasonic couplers are made from titanium, carbon steel, stainless steel, or a combination thereof.

9. The ultrasonic coupler assembly of claim 7, wherein the height of the first ultrasonic coupler and the height of the second ultrasonic coupler are both greater than the thickness of the pipe by a factor between at least five to about fifteen.

10. The ultrasonic coupler assembly of claim 7, wherein the first location and the second location are about 180 degrees around the pipe apart.

11. The ultrasonic coupler assembly of claim 7, wherein the first location and the second location are less than 180 degrees around the pipe apart.

12. The ultrasonic coupler assembly of claim 7, wherein each of the first and second ultrasonic transducers is configured to emit ultrasonic signals that are detected by the other one of the first and second ultrasonic transducers.

13. The ultrasonic coupler assembly of claim 7, wherein the respective lengths of the first and second ultrasonic couplers are parallel with a longitudinal axis of the pipe.

14. An ultrasonic coupling system comprising:
a plurality of pairs of couplers, each of the couplers having a first side and a second side opposite the first side, the first side of each coupler configured to be coupled to an exterior of a wall of a pipe along the full length of the first side, wherein each coupler has a respective height, as measured between first and second surfaces thereof, that is greater than a thickness of the pipe by a factor of at least five, and each coupler has a respective length transverse to the respective height and greater than the respective height; and
a plurality of ultrasonic transducers, each attached to the second side of a respective one of the couplers, wherein the ultrasonic transducers that are coupled to the respective ones of the couplers in one of the plurality of pairs of couplers are configured to emit and receive ultrasonic signals between themselves when the respective ones of the couplers are coupled to the exterior surface of the pipe, and wherein a distance between the first and second sides of each of the respective ones of the couplers is less than a length of its first side.

15. The ultrasonic coupling system of claim 14, wherein the distance between the first and second sides of each of the couplers is greater than a thickness of the pipe by a factor of at least five.

16. The ultrasonic coupling system of claim 14, wherein each of the pairs of couplers are configured to be coupled to the pipe at locations that are less than 180 degrees around the pipe apart.

17. The ultrasonic coupling system of claim 16, wherein each of the pairs of couplers are configured to be coupled to the exterior surface of the pipe such that a longer dimension of the first side of each of the couplers is parallel to a longitudinal axis of the pipe.

* * * * *